US00PP15039P2

(12) United States Plant Patent
Bevelander

(10) Patent No.: US PP15,039 P2
(45) Date of Patent: Jul. 27, 2004

(54) HIBISCUS PLANT NAMED 'BOSTON'

(50) Latin Name: *Hibiscus rosa-sinensis*
Varietal Denomination: Boston

(75) Inventor: Marinus Jacobus Bevelander, Amstelveen (NL)

(73) Assignee: Cooperatieve Vereniging Werk groep Hibiscus U.A., Rijsenhout (NL)

( * ) Notice: Subject to any disclaimer, the term of this patent is extended or adjusted under 35 U.S.C. 154(b) by 0 days.

(21) Appl. No.: 10/600,792

(22) Filed: Jun. 20, 2003

(51) Int. Cl.[7] ..... A01H 5/00
(52) U.S. Cl. ..... Plt./257
(58) Field of Search ..... Plt./257

*Primary Examiner*—Anne Marie Grunberg
*Assistant Examiner*—June Hwu
(74) *Attorney, Agent, or Firm*—C. A. Whealy

(57) ABSTRACT

A new and distinct Hibiscus plant named 'Boston', characterized by its compact, upright and uniform plant habit that is appropriate for container production; freely branching habit; glossy dark green leaves; freely and continuous flowering habit; light orange-colored flowers; and good resistance to flower bud abscission.

1 Drawing Sheet

Botanical classification/cultivar designation: *Hibiscus rosa-sinensis* cultivar Boston.

BACKGROUND OF THE INVENTION

The present invention relates to a new and distinct cultivar of Hibiscus, botanically known as *Hibiscus rosa-sinensis*, and hereinafter referred to by the name 'Boston'.

The new Hibiscus is a naturally-occurring whole plant mutation of the *Hibiscus rosa-sinensis* cultivar Charleston, disclosed in U.S. Plant Pat. No. 14,216. The cultivar Boston was discovered and selected by the Inventor as a flowering plant within a population of plants of the cultivar Charleston in a controlled environment in Amstelveen, The Netherlands, in 2000.

Asexual reproduction of the new Hibiscus by vegetative terminal cuttings taken in a controlled environment in Amstelveen, The Netherlands, since 2000, has shown that the unique features of this new Hibiscus are stable and reproduced true to type in successive generations.

SUMMARY OF THE INVENTION

The cultivar Boston has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Boston'. These characteristics in combination distinguish 'Boston' as a new and distinct cultivar:

1. Compact, upright and uniform plant habit that is appropriate for container production.
2. Freely branching habit.
3. Glossy dark green leaves.
4. Freely and continuous flowering habit.
5. Light orange-colored flowers.
6. Good resistance to flower bud abscission.

Plants of the new Hibiscus are most similar to plants of the cultivar Charleston. In side-by-side comparisons conducted in Amstelveen, The Netherlands, plants of the new Hibiscus differed from plants of the cultivar Charleston primarily in flower color as plants of the cultivar Charleston had red-colored flowers.

BRIEF DESCRIPTION OF THE PHOTOGRAPH

The accompanying colored photograph illustrates the overall appearance of the new Hibiscus, showing the colors as true as it is reasonably possible to obtain in colored reproductions of this type. Colors in the photograph may differ slightly from the color values cited in the detailed botanical description which accurately describe the colors of the new Hibiscus.

The photograph comprises a side perspective view of a typical flowering plant of 'Boston' grown in a container.

DETAILED BOTANICAL DESCRIPTION

The aforementioned photograph and following observations and measurements describe plants grown in Amstelveen, The Netherlands, grown in 15-cm container in a glass-covered greenhouse during the spring and summer under conditions which closely approximate commercial production. During the production of the plants, day and night temperatures ranged from 15 to 25° C. and light levels were about 500 kilolux. Plants were about two years old when the photograph and the description were taken. In the description, color references are made to The Royal Horticultural Society Colour Chart, 1986 Edition, except where general terms of ordinary dictionary significance are used.

Botanical classification: *Hibiscus rosa-sinensis* cultivar Boston.

Parentage:

Naturally-occurring whole plant mutation of the *Hibiscus rosa-sinensis* cultivar Charleston, disclosed in U.S. Plant patent application Ser. No. 10/259,961.

Propagation:

*Type.*—By vegetative terminal cuttings.

*Time to initiate roots.*—About 25 days at a temperature of 23° C.

*Time to produce a rooted young plant.*—About 40 days at a temperature of 22° C.

*Root description.*—Thick; whitish in color.

*Rooting habit.*—Moderately vigorous; freely branching.

Plant description:

*Plant form and growth habit.*—Compact, upright and uniform plant habit; appropriate for container production. Vigorous growth habit.

*Branching habit.*—Freely branching, usually about three or four lateral branches.

*Plant height.*—About 25 cm.

*Plant diameter* (*area of spread*).—About 40 to 45 cm.

*Lateral branch description.*—Length: About 10 cm. Diameter: About 8 mm. Internode length: About 2 to 2.5 cm. Texture: Smooth, glabrous. Color: Close to 200C.

*Foliage description.*—Arrangement: Alternate, simple. Length: About 8 cm. Width: About 5.5 cm. Shape: Roughly cordate. Apex: Acuminate. Base: Cordate. Margin: Irregularly serrate. Texture, upper and lower surfaces: Glabrous; leathery. Venation pattern: Pinnate. Color: Young leaves, upper and lower surfaces: 146A; glossy. Fully expanded leaves, upper surface: Darker than 147A; glossy. Fully expanded leaves, lower surface: 147A. Venation, upper and lower surfaces: 146A. Petiole: Length: About 3 cm. Diameter: About 3 mm. Texture, upper and lower surfaces: Smooth, glabrous. Color, upper and lower surfaces: Darker than 147A.

Flower description:

*Flower arrangement/appearance.*—Rounded flowers arranged singly at terminal leaf axils. Freely and continuous flowering with usually about five to six flower buds and/or open flowers per terminal apex. Flowers face mostly upright. Flowers are open for about one day. Flowers persistent. Flowers not fragrant.

*Natural flowering season.*—Usually spring and summer or during periods of warm weather.

*Flower diameter.*—About 8 cm.

*Flower length* (*height*).—About 4 cm.

*Flower bud* (*just before showing color*).—Resistance to abscission: Plants of the new Hibiscus have been observed to resist flower bud drop. Length: About 4 to 5 cm. Diameter: About 1 to 1.5 cm. Shape: Oblong, elliptical. Color: 147A.

*Petals.*—Arrangement: Corolla consists of five petals that are overlapping towards apex. Length: About 6 to 7 cm. Width: About 5 to 6 cm. Shape: Spatulate or fan-shaped. Apex: Rounded. Base: Attenuate. Margin: Weakly serrated. Texture, upper and lower surfaces: Smooth, glabrous, satiny. Color: When opening and fully opened, upper surface: 22A. When opening and fully opened, lower surface: 22A to 22C. Throat: 53A.

*Sepals.*—Appearance: Five or six sepals fused into a tubular star-shaped calyx. Length: About 2 cm. Width: About 1 cm. Shape: Narrowly oblong. Apex: Acute. Base: Fused. Margin: Entire. Texture, upper and lower surfaces: Smooth. Color, upper and lower surfaces: Close to 146A.

*Peduncles.*—Length: About 7 mm. Diameter: About 3 mm. Angle: Mostly upright. Strength: Strong, rigid. Texture: Smooth. Color: Darker than 146A.

*Reproductive organs.*—Androecium: Stamen number: Numerous, about 60 per flower. Anther shape: Globular. Anther length: About 1 mm. Anther color: 12A. Amount of pollen: Abundant. Pollen color: Close to 15A. Gynoecium: Pistil number: One per flower. Pistil length: About 6 to 7 cm. Style length: About 4 to 5 cm. Style texture: Smooth, waxy. Style color: Towards base, 53A; mid-section and towards apex, 33A. Stigma appearance: Five, rounded. Stigma color: Close to 44A. Ovary color: Close to 154C to 154D.

*Fruit/seed.*—Fruit and seed production has not been observed.

Disease/pest resistance: Plants of the new Hibiscus have not been observed to be resistant to pathogens and pests common to Hibiscus.

It is claimed:

1. A new and distinct Hibiscus plant named 'Boston', as illustrated and described.

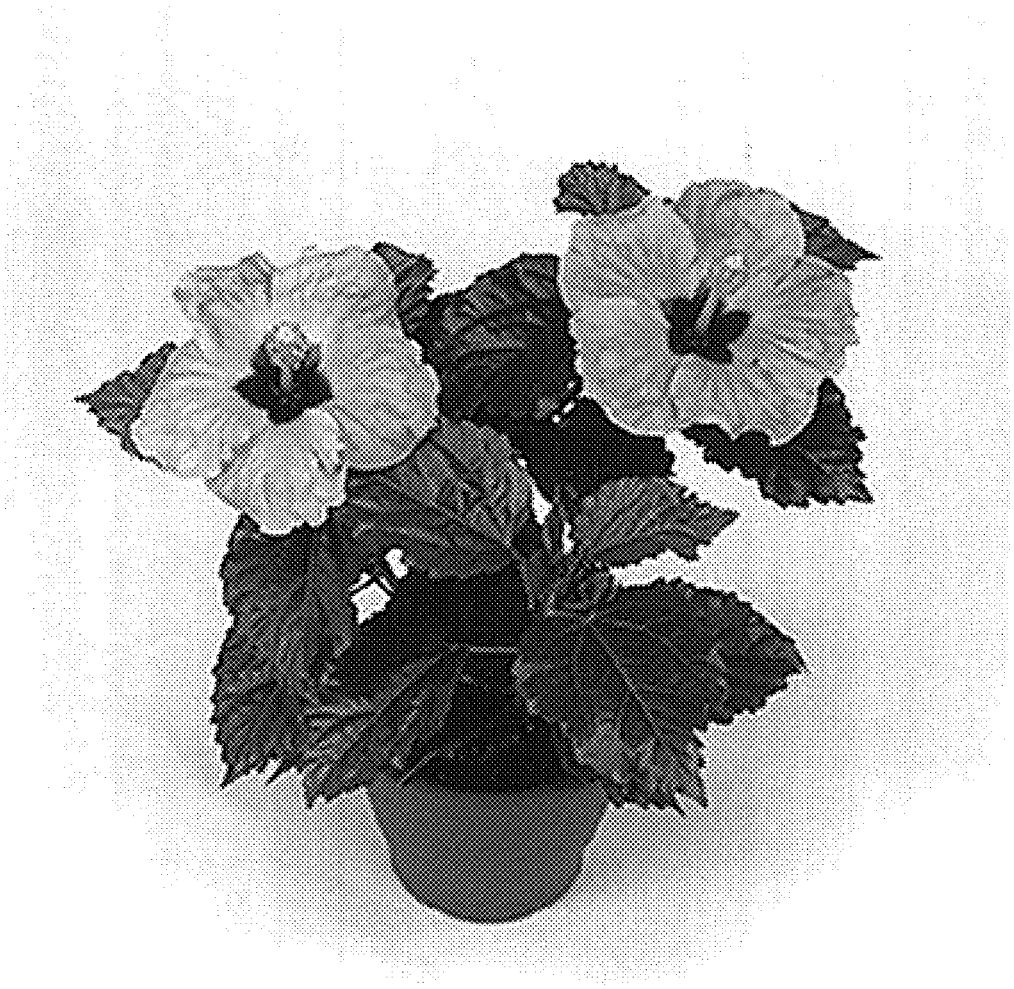

* * * * *